United States Patent
Selve

(10) Patent No.: US 10,197,478 B2
(45) Date of Patent: Feb. 5, 2019

(54) SAMPLE CARRIER AND METHOD FOR PROCESSING A SAMPLE

(71) Applicant: TECHNISCHE UNIVERSITÄT BERLIN, Berlin (DE)

(72) Inventor: Sören Selve, Berlin (DE)

(73) Assignee: Technische Universitat Berlin, Berlin (DE)

( * ) Notice: Subject to any disclaimer, the term of this patent is extended or adjusted under 35 U.S.C. 154(b) by 101 days.

(21) Appl. No.: 15/303,482

(22) PCT Filed: Apr. 10, 2015

(86) PCT No.: PCT/EP2015/057877
§ 371 (c)(1),
(2) Date: Dec. 13, 2016

(87) PCT Pub. No.: WO2015/155347
PCT Pub. Date: Oct. 15, 2015

(65) Prior Publication Data
US 2017/0097291 A1   Apr. 6, 2017

(30) Foreign Application Priority Data

Apr. 11, 2014   (DE) .......................... 10 2014 005 689

(51) Int. Cl.
| | |
|---|---|
| *B24B 41/06* | (2012.01) |
| *B24B 1/00* | (2006.01) |
| *G01N 1/32* | (2006.01) |
| *B24B 47/04* | (2006.01) |
| *B24B 47/12* | (2006.01) |
| *B24B 7/02* | (2006.01) |

(Continued)

(52) U.S. Cl.
CPC ............. *G01N 1/32* (2013.01); *B23Q 1/4828* (2013.01); *B23Q 5/34* (2013.01); *B24B 7/02* (2013.01); *B24B 7/04* (2013.01); *B24B 7/16* (2013.01); *B24B 41/067* (2013.01); *B24B 47/04* (2013.01); *B24B 47/12* (2013.01)

(58) Field of Classification Search
CPC .................................. B24B 1/00; B24B 41/06
USPC .................... 451/364, 393, 392, 150, 41, 28
See application file for complete search history.

(56) References Cited

U.S. PATENT DOCUMENTS 3,105,330 A * 10/1963 Grage .................... B23Q 3/103
269/286

FOREIGN PATENT DOCUMENTS

| CN | 1726116 A | 1/2006 |
|---|---|---|
| DE | 10 2009 052 250 A1 | 5/2011 |

(Continued)

OTHER PUBLICATIONS

International Search Report and Written opinion of corresponding PCT/EP2015/057877, dated Sep. 1, 2015, 13 pages.

*Primary Examiner* — Robert Rose
(74) *Attorney, Agent, or Firm* — Lewis Roca Rothgerber Christie LLP

(57) ABSTRACT

The invention relates to a sample carrier for a sample (70). Said sample carrier comprises a supporting base (10), a carriage (20) having a receiving region (30) for the sample (70), the carriage (20) being supported on the supporting base (10), a guide (40), the carriage (20) being movably arranged along the guide (40), and a disc (60) that is rotationally movable about an axis of rotation (50), said disc being operatively connected to the carriage (20), wherein a center (65) of the disc (60) is located outside of the axis of rotation (50).

11 Claims, 5 Drawing Sheets

(51) Int. Cl.
*B24B 7/04* (2006.01)
*B24B 7/16* (2006.01)
*B23Q 5/34* (2006.01)
*B23Q 1/48* (2006.01)

(56) References Cited

FOREIGN PATENT DOCUMENTS

JP  2008-290192  12/2008
JP  2010-194637   9/2010

* cited by examiner

SAMPLE CARRIER AND METHOD FOR PROCESSING A SAMPLE

CROSS-REFERENCE TO RELATED APPLICATION(S)

This application is a National Phase Patent Application and claims priority to and the benefit of International Application Number PCT/EP2015/057877, filed on Apr. 10, 2015, which claims priority to German Patent Application Number 10 2014 005 689.9, filed on Apr. 11, 2014, the entire contents of all of which are incorporated herein by reference.

The invention relates to a sample carrier and a method for processing a sample. In particular, the present invention relates to a sample carrier for the preparation of suitable samples for transmission electron microscopy (TEM) or other analysis techniques based on thin-film samples such as scanning electron microscopy (SEM).

TECHNOLOGICAL BACKGROUND OF THE INVENTION

TEM specimens usually have thicknesses of a few nanometers so as to be transparent to electrons. Different preparation techniques can be used depending on the material to be examined and the problems to be solved. Conventional methods hereby include applying a nanoscale suspension on special TEM grids as well as powder preparation, wherein the sample to be tested is present as a finely atomized powder material. Another possibility for preparing extremely thin layers is based on cleavable or cuttable sample materials. Thin layers of a crystalline material along the lattice planes of a material can be produced with the so-called small-angle cleavage technique (SACT), whereas for example with ultra-microtomy amorphous biological samples embedded in a casting resin can initially be brought into a solid, cuttable form and subsequently surface-machined in an ultra-microtome.

The aforementioned methods are supplemented by various methods for selective thinning of individual material regions of the samples. This thinning can be done in various ways, wherein electrolytic thinning is widely used for metallic materials. Chemical etching or processing with a focused ion beam (FIB) is also common. For many materials, purely mechanical methods, for example methods using fine grinding and fine polishing discs, optionally with the aid of a polishing agent, can also be used.

Over the past years, many of these methods have been constantly improved and optimized. In addition to commercially available special equipment for thinning, tools for manual mechanical fine polishing processing are also known. However, all prior art methods use ion thinning for final fine polishing of the produced thin-film sample surfaces, with the exception of ultra-microtomy, cleaving and electrolytic thinning. However, this partly causes considerable amorphization of existing crystalline regions. These amorphous layers produce, inter alia, severe noise in the TEM images. Depending on the material, the electron beam may also cause recrystallization which makes it considerably more difficult to interpret the examined object. It is therefore the aim of any type of sample preparation to prevent the formation of such amorphous layers. Furthermore, the additional ion bombardment and etching introduces unwanted artifacts which may make it much more difficult to interpret the TEM results.

Although a sample surface prepared by ion thinning has extremely small surface roughness, this process should not be used because of these problems. Although the aforementioned cleaving and cutting process can make the additional use of ion thinning (or FIB in particular) largely unnecessary, it cannot be used with all types of samples and have severe limitations for spatially resolved investigations. Accordingly, various mechanical abrasion processes are particularly advantageous for the vast majority of samples.

One of the most common polishing methods is mechanical thinning of samples by using a machine having a rotating grinding wheel placed on the sample. In order to produce an optimal homogenous material removal, the sample is additionally continuously rotated under the abrasion spot, so that the thinned region forms a concave trough profile. The size of the produced troughs depends mainly on the size and thickness of the grinding wheel and its position relative to the sample surface.

However, when using such trough grinders, the sample spots thinned with such a trough grinder have disadvantageously an inhomogeneous thickness, so that an ideal image can be formed with TEM only within a very small area around the trough center or the inner trough edge. Such a process is very time consuming, in particular for spatially resolved studies on specific regions of material samples due to the considerable effort associated with the preparation. Moreover, it often impossible to deliberately prepare the desired locations especially of inhomogeneous samples.

The invention is therefore based on the object to provide a sample carrier for thinning by way of machine-based mechanical fine polishing, which obviates or at least significantly ameliorates one or more of the aforedescribed problems of the prior art in the preparation of suitable samples for transmission electron microscopy (TEM). In particular, a method for thinning specimens for TEM is to be provided, which generally does not require the use of FIB or ion thinning and which also allows, as a result of large-scale removal of material, a spatially resolved examination of inhomogeneous samples following only a single preparation step.

SUMMARY OF THE INVENTION

The aforementioned object is attained by using the sample carrier according to the invention of claim 1. The invention provides a sample holder for a sample. This sample holder includes a supporting base, a carriage having a receiving region for the sample, wherein the carriage is supported on the supporting base, a guide, wherein the carriage is arranged for movement along the guide, and a disc which is rotatable around an axis of rotation and operatively connected to the carriage, wherein a center of the disc is located outside the axis of rotation.

This center may be in particular the geometric center of the disc, which can be calculated mathematically by averaging the spatial position of all edge points of the disc. In inhomogeneous plate-shaped materials, the geometric center may differ significantly from the center of mass of the disc. With a skillfully arranged composition of the disc materials, especially the axis of rotation of the rotatable disc and the principal axis of inertia of the disc through the center of mass can be merged to avoid an imbalance.

The invention is based on the observation that although the troughs produced with a conventional trough grinder have a sufficiently low surface roughness due to the employed fine grinding process, hence avoiding the use of thinning by ion thinning, the commonly employed sample rotation allows only point-wise processing, i.e. forming troughs through abrasion. However, when the underlying grinding operation is performed not on the basis of such a circular or elliptical movement, but when this grinding operation is performed instead from a linear movement, the resulting grinding profile is predominantly wedge-shaped with an extended edge corresponding to the range of movement of the employed sample holder.

In a preferred embodiment of the invention, a rotatably mounted and rotationally driven drive wheel is in direct or indirect operative connection with a rotatable disc, so that the preferably symmetric rotary movement of the drive wheel is translated into an eccentric rotation of the rotatable disc, with both components having a common axis of rotation. The drive wheel may have a conical shape to allow for a more accurate positioning of the sample carrier. The rotatable disc may preferably be a circular disc rotating outside its geometric center. In another preferred variant, the rotatable disc may have an elliptical shape. The axis of rotation may be located inside or outside of the two foci. In another preferred variant of the rotatable disc, its outer contour may correspond to any freeform shape. If the drive itself can already provide the desired eccentric movement, then an additional rotatable disc can be dispensed with. The exact nature of the operative connection between the drive wheel and the rotatable disc can thereby be adapted to specific requirements of the structure. In a preferred variant, the operative connection represents a magnetic interaction between the two components. To this end, the rotatable disc and/or the drive wheel are at least partially made of a magnetic or magnetizable material. This enables accurate positioning and a fixed, but releasable connection between the individual components. Preferably, both the drive wheel and the rotatable disc each have a uniform thickness in the mm range (preferably between 1 and 50 mm, more preferably between 1 and 25 mm, and even more preferably between 1 and 10 mm, and most preferably between 1 and 5 mm). The lateral extent of the two rotary members is approximately identical and preferably lies in the centimeter range (preferably between 1 and 50 cm, more preferably between 1 and 20 cm, even more preferably between 1 and 10 mm, and most preferably between 1 and 3 cm).

Particularly preferred is a size ratio of the maximum lateral dimensions of the drive wheel and the rotatable disc between 0.2 and 5 (more preferably between 0.5 and 2). Preferably, the top and/or bottom sides of the drive wheel and/or of the rotatable disc are completely flat.

According to the invention, the rotatable disc is at least partially enclosed by a stationary supporting base, in which a movable carriage is directly or indirectly supported by a corresponding guide. This guide may be, for example, a simple sliding bearing or a rolling bearing. The carriage is in turn in direct or indirect operative connection with the rotatable disc, so that the preferable eccentric rotation of the disc is translated by this operative connection into the oscillatory movement or three-dimensional trajectory defined by the guide of the supporting base. Particularly preferred is a direct operative connection by frictional coupling mainly between the points on the rotatable disc having the greatest distance from the axis of rotation and the bottom edges of the carriage oriented perpendicular to the movement direction of the carriage. In a particularly preferred embodiment, the rotational movement of the drive wheel is translated by the eccentrically rotating rotatable disc into a linear movement of the carriage in a plane. In another preferred variant, the movement may deviate from a purely linear form, so that, for example, additional oscillations transverse to the movement direction of the carriage can be superimposed. In another preferred embodiment, according to the invention, the direction and velocity of the generated translational movement also can be influenced by matching the outer contours of the rotatable disc as freeform or in an alternative embodiment by an indirect operative connection between rotatable disc and bottom surface of the carriage. Although the materials for the supporting base, the guide and the carriage can be freely selected as required, an embodiment made of metallic materials is preferred. In the case of a magnetic operative connection between the rotary elements, this embodiment should preferably have non-magnetic properties.

Preferably, a receiving region for a sample pad configured to receive the sample is located in the top part of the carriage. This receiving region may have an opening in exact registration with a corresponding sample pad so that preferably a portion of the sample pad protrudes from the opening of the carriage. In this way, both the carriage and the sample are protected from accidental contamination by foreign materials abraded during polishing.

In a particularly preferred embodiment, the sample pad is formed entirely of an optically transparent material, in particular silicate glass or borosilicate glass. Optically transparent hereby indicates a high transmissivity of $T>10\%$, preferably $T>50\%$, particularly preferably $T>90\%$, for electromagnetic radiation in certain regions of the spectral region between ultraviolet (UV) and infrared (IR), but in particular in the range of the visible spectrum (380-760 nm). Furthermore, in this preferred embodiment of the invention at least one opening is disposed in each of the supporting base, in the rotatable disc and in the drive wheel, generating a common line of sight through which radiation from below can pass through the sample located on the transparent sample pad specimen for integrated process control for microscopy purposes.

The samples are thinned according to the invention by using a mechanical grinding or polishing unit, wherein a rotating grinding wheel abrasively engages with the test specimens above the sample surface. In a preferred embodiment of this arrangement, the axis of rotation of the grinding wheel points in the direction of movement of the carriage; in another preferred embodiment, this axis of rotation may enclose an angle with the direction of movement of the carriage. Preferably, these angles are less than 50°, particularly preferred are angles less than 10°.

The sample holder according to the invention is designed for use with various solid materials as the sample body. Here, all materials used for the conventional trough grinding can typically be used. These samples may be composed of, for example, (bulk)-Si, —LiFePO$_4$ and —GaP. Other (bulk)-sample materials are, for example, GaAs (crystalline, soft, brittle), sapphire (crystalline, hard), and SiO$_2$ (amorphous).

In another preferred embodiment of the invention, the axes of rotation of the rotary driven drive wheel and of the rotatable disc that is directly or indirectly operatively connected with the drive wheel may differ from each other. However, the same functional relationships between the individual components of the sample holder exist in this embodiment. The aforedescribed operative connection between the two rotary components may be implemented, for example, by way of a meshing gear tooth pattern or another type of coupling constructed of belts, rollers or corresponding linkage. Such operative connection allows greater flexibility in the design of the movement transformation according to the invention; in particular, the rotational speeds may be stepped up or stepped down and/or a corresponding stepped or continuously variable transmission may be provided between the elements.

In another preferred embodiment of the invention, after providing a sample on a sample pad, the sample is moved translationally in a first plane and ground, wherein a grinding unit is moved in a second plane, with the second plane enclosing an angle greater than 50° with the first plane. The sample prepared by this method can be examined directly by TEM and additional processing steps (which would be required in conventional processes) can be omitted. In particular, there is no need for further thinning or fine-polishing by ion thinning or FIB prior to TEM examination.

According to one aspect of the present invention, a wedge grinding attachment (also referred to as a sample carrier) is disclosed which can be used to assist with the preparation of transmission-electron-microscopy specimens of solids. By using the wedge grinding attachment, samples can be prepared that do not require further ion beam etching. Since the existing conventional preparation aids can be used, the attachment is designed to enable this with minimum effort. For example, no changes are required for a conventional dimple grinder (also referred to as a grinding unit), only the height of the standard glass carriers (Pyrex) (diameter=10 mm, height=10 mm) must be adjusted. In order to convert the rotation of the table (also referred to as a rotatable drive wheel) into a translational movement, an eccentric wheel (also referred to as a rotatable disc) is placed on the turntable (also referred to as a rotatable drive wheel) of the dimple grinder. This eccentric wheel engages with the sample table of the wedge grinding attachment (also referred to as a carriage), pushing the carriage back and forth.

This is necessary to prevent the formation of grinding grooves and to uniformly and smoothly remove material. Depending on the position of the eccentric wheel, the excursion of the table movement can be adjusted to match the sample size. The turntable (also referred to as rotatable drive wheel) of the dimple grinder is strongly ferromagnetic so as to readily retain an eccentric wheel made of plain steel, which can thus be positioned and does not shift during processing. The entire structure of the attachment fits on the conical base of the dimple grinder and can hence be easily removed and replaced again without losing the previously established settings.

Alignment marks on the sample stage and on the glass substrate (also referred to as a sample pad) enable simple positioning of the sample material, so that the sample material is always at the location where it comes into contact with the grinding wheel. A groove would be formed on the sample as a result of the longitudinal movement of the table under the rotating grinding wheel. One side would thereby be abraded "in the direction of rotation", the other side "against the direction of rotation". Fragments from the sample area located in the opposite direction would then break away and scratch the entire sample or even destroy the sample. Accordingly, the grinding wheel must always operate directly on the edge the sample, to prevent fragments from detaching.

Whether the desired sample area is already polished sufficiently thin can be easily checked photo-optically for standard materials such as silicon based on the red coloration. For this purpose, the sample table has a hole (also referred to as opening of the carriage) as well as the eccentric wheel (also known as opening of the rotatable disc) to be able to use the light of the transmitted light source disposed in dimple grinder. Materials with thicknesses in the nanometer range also show interference lines, which are easily observable in the light microscope. For these necessary checks, the glass substrate including the sample can be removed and examined, and thereafter be inserted again at the same location along the positional marks and further processed if necessary. If the sample is thin at the desired locations, it is detached from the glass support, thereafter purified, and can already be examined in the TEM.

First test samples of (bulk)-Si, —LiFePO$_4$ and —GaP were prepared by using a prototype of the wedge grinding attachment and the conventional Gatan Dimpler Model 656. The preparation of water-containing polishing slurries may in the case of Si result in the formation of a strongly amorphous layer due to the formation of SiO$_2$ on the surface. Accordingly, no water-based polishing slurries should be used for easily oxidizable materials.

An inadequately cleaned surface can also cause the formation of severe contamination under electron beam exposure in GaP. However, this can be easily avoided by a few minutes of plasma cleaning—a step which is recommended for most samples and which has no adverse effect on the structure of the sample due to the employed low electron energy. In spite of the aforementioned shortcomings, regions were found in all samples that are suitable and thin enough for high resolution images (HRTEM). The HRTEM images were obtained with a conventional TECNAI G$^2$20 with an acceleration voltage of 200 kV and a LaB$_6$ emitter. The resolution limit of the device is 0.2 nm and is therefore extremely well suited for evaluating the high resolution capabilities, since the typical structural features have precisely this dimension—when the sample is poor, no structures can be identified in the TEM.

Other materials of different hardness and crystallinity can be used, for example, GaAs (crystalline, soft, brittle), sapphire (crystalline, hard), SiO$_2$ (amorphous) and several polycrystalline metals and alloys.

The wedge grinding attachment has other preferred embodiment variants.

A slight oscillation of the sample of a few degrees during grinding and polishing can have a positive effect on the polish. The base of the attachment should have a variable diameter so as to be able to match different production-related base diameters of a grinding unit (e.g. of the Gatan Dimple-Grinder).

Another embodiment of the eccentric wheel can increase the velocity at which the table moves laterally and can thus reduce the residence time of the grinding wheel at the respective points of reversal of the table, resulting in a more uniform material removal. Eccentric wheels with varying degrees of eccentricity may allow the production of samples with different sizes (in the mm range).

The wedge grinding attachment according to the invention may be used, for example, by sample preparation laboratories that use a conventional grinding unit such as the Gatan Dimple Grinder Model 656. The wedge grinding attachment extends the function of the conventional grinding unit by offering the possibility of customizing wedge cuts and dispensing with ion beam etching which affects the material. Applications in a non-TEM technical field are also conceivable. Since the scanning electron microscope (SEM) also benefits from ultrathin samples (smaller region of interaction of the electron beam and thus better lateral resolution), the wedge grinding attachment according to the invention can advantageously be used here too.

Other preferred embodiments of the invention result from the additional features recited in the dependent claims.

The various embodiments of the invention mentioned in this application can advantageously be combined, unless stated otherwise in individual cases.

BRIEF DESCRIPTION OF THE FIGURES

The invention will now be described in form of exemplary embodiments and with reference to the accompanying drawings. These show in:

FIG. 1b a schematic sectional view of the sample holder according to FIG. 1a;

DETAILED DESCRIPTION OF THE INVENTION

Figure 1A:
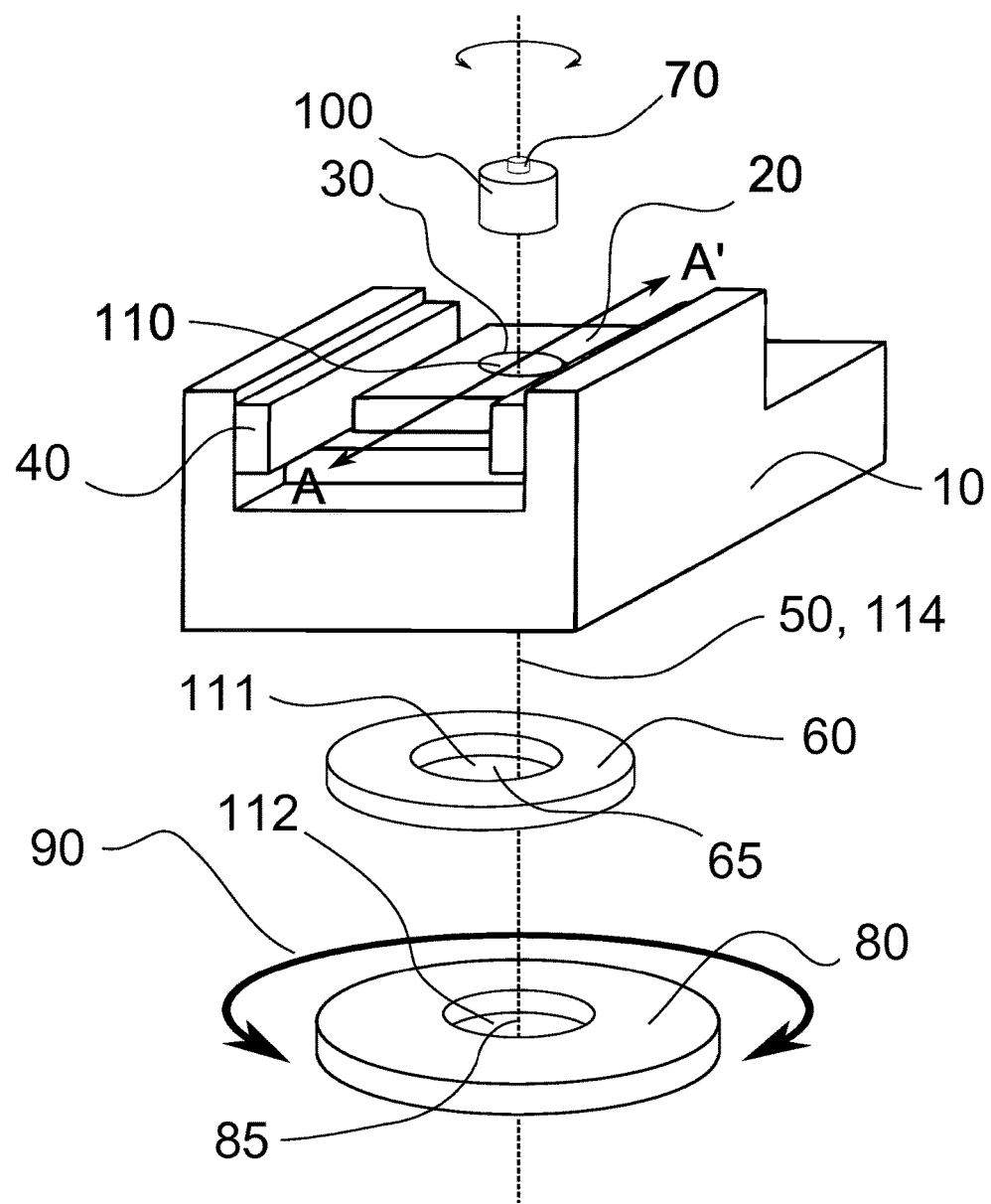
FIG. 1a a schematic exploded view of a sample holder according to the invention for a sample 70 with a single axis of rotation 50.
Figure 1B:
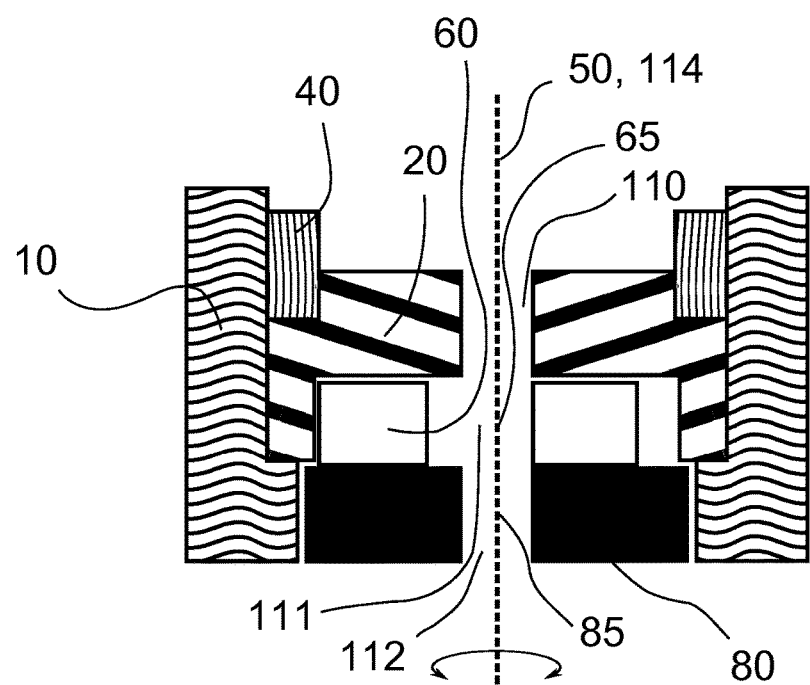

FIG. 1a shows a schematic exploded view of a sample holder according to the invention for a sample 70 having a single axis of rotation 50. The rotatable drive wheel 80 is rotatably supported on the axis of rotation 50 for rotation around a center, here the geometric center 85 of the circular drive wheel 80, and operatively connected to a rotary drive 90. The type of this operative connection is variable and may be, for example, a belt or gear drive. The drive wheel 80 is in direct operative connection with the rotatable disc 60, i.e. both discs are arranged one above the other and are in direct contact with each other. The type of this operative connection is also variable; however, a fixed, but optionally releasable magnetic connection exists between the two elements 60, 80. Alternatively, this operative connection may be designed as friction or adhesive coupling. A characteristic feature of this embodiment is that a center 65 of the rotatable disc 60, in particular its geometrical center, is located outside the common axis of rotation 50. In this exemplary embodiment, the shape of the disc 60 is circular, while other shapes, for example elliptical or as a freeform, are also possible. Because the axis of rotation 50 is positioned outside of a center 65 of the disc 60, preferably at a distance of greater than 1%, particularly preferably greater than 10%, of the maximum lateral extent of the disc 60, the apparent radius depends on a direction or rotation angle relative to the axis of rotation 50. A rotation-angle-dependent coupling to a preferably linearly operating adjustment element can be attained via this asymmetry. The disc 60 is at least partially enclosed by a fixed supporting base 10 in which a movable carriage 20 is supported by way of a guide 40. This guide may be, for example, a simple sliding bearing or a rolling bearing. The movable carriage 20 is operatively connected to the disc 60 via a preferably direct impact coupling so that in particular a rotating rotary movement of the disc 60 is translated into in a linear oscillating movement of the carriage 20 along the direction A-A'. To attach the sample 70, a receiving region 30, which is formed of a circular opening 110 of the carriage 20 and in which a sample pad 100 with a sample 70 placed thereon can be inserted with an exact fit, is disposed in the carriage 20. In this case, a portion of the sample pad disposed above the carriage 20 may also at least partially protrude from the surface to protect the carriage 20. To enable imaging of the grinding process during the preparation processes, the sample pad 100 in this embodiment may be made of a material that is optically transparent in at least one spectral range so as to form a continuous linear viewing channel 114 (here identical with the common axis of rotation 50) composed of respective openings 110, 111, 112 in the carriage 20, in the supporting base 10 (not visible) in the disc 60 and in the drive wheel 80, through which for example the sample 70 can be illuminated for detailed microscopic examination during preparation. FIG. 1b shows a schematic sectional view of the sample holder according to the invention corresponding to the embodiment according to FIG. 1a. The depicted sectional view passes through the axis of rotation 50 and is perpendicular to the plane spanned by the axis of rotation 50 and the direction A-A'. The association of the reference numerals with the individual components corresponds largely to the description of FIG. 1a. The sample pad 100 and the sample 70 are not explicitly shown in FIG. 1b for sake of clarity.

Figure 2:
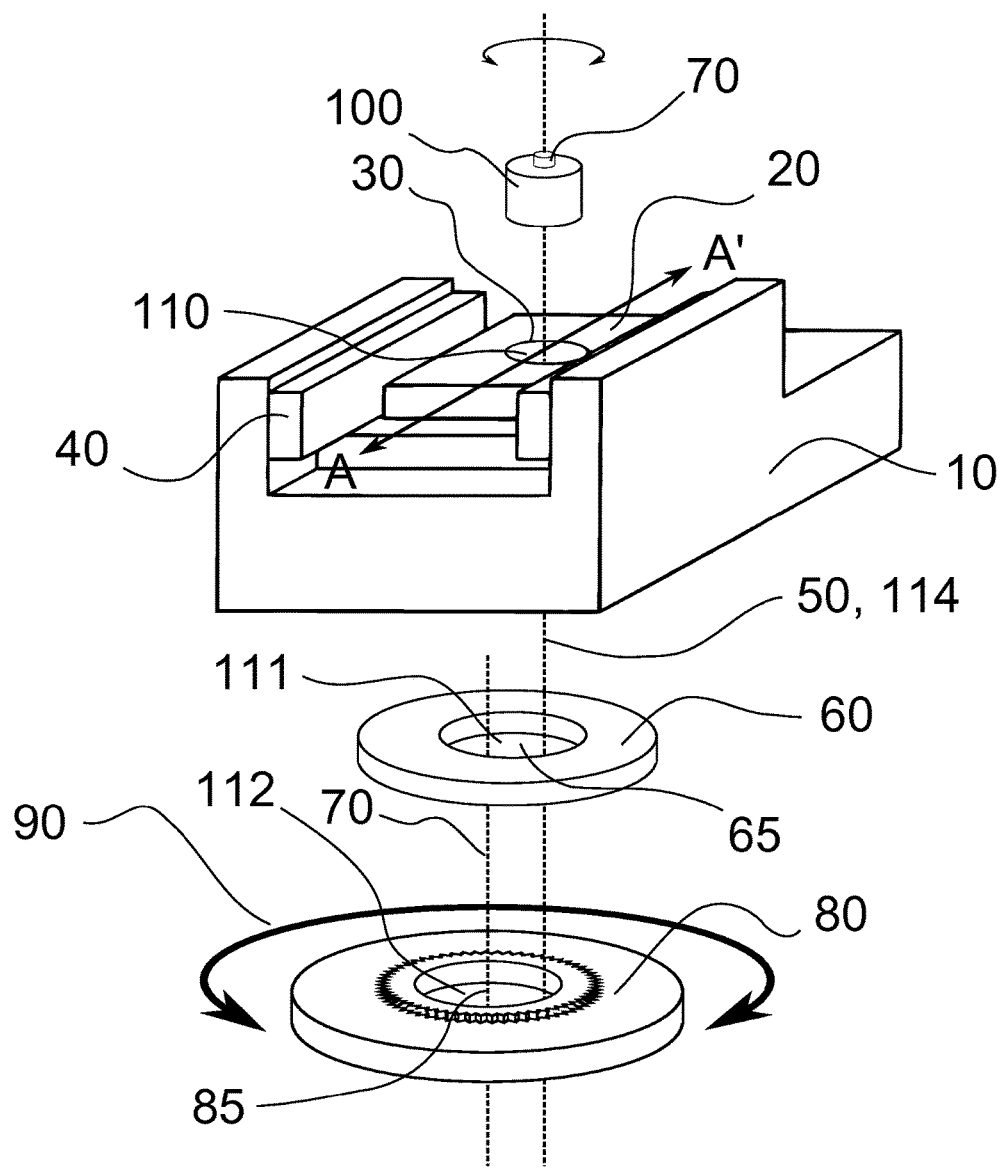
FIG. 2 a schematic exploded view of a sample holder according to the invention for a sample 70 with two-fold axis of rotation 50, 75.

FIG. 2 shows a schematic exploded view of a sample holder according to the invention for a sample 70 with a two-fold axis of rotation 50, 75. The association of the reference numerals as well as of the functional relationships of the individual components corresponds largely to the description of FIGS. 1a and 1b. A significant difference in this exemplary embodiment is the presence of a second axis of rotation 75, which passes through the geometric center 85 of the drive wheel 80. The drive wheel 80 and the disc 60 are operatively connected here by way of example via a gear connection between the two elements. In particular, this enables in a simple way a conversion between the velocities of the individual rotary movement. The continuous view channel 114 for sample illumination is here made possible by a corresponding overlap of the openings 110, 111, 112 in the carriage, the supporting base 10 (not visible), in the disc 60 and in the drive wheel 80. Also for this exemplary embodiment, the diagram is selected for better identifying the relationships such that the axis of rotation 50 precisely coincides with the center of the sample receiving region 30. However, this does not limit how the individual components are positioned relative to one another and may deviate therefrom depending on the circumstances or requirements. By suitable design of the operative connection between the carriage 20 and the disc 60, the positioning of the elements may significantly different from the illustrated diagram. In particular, for example, the second axis of rotation 75 may then be made to coincide with the center of the sample receiving region 30.

Figure 3:
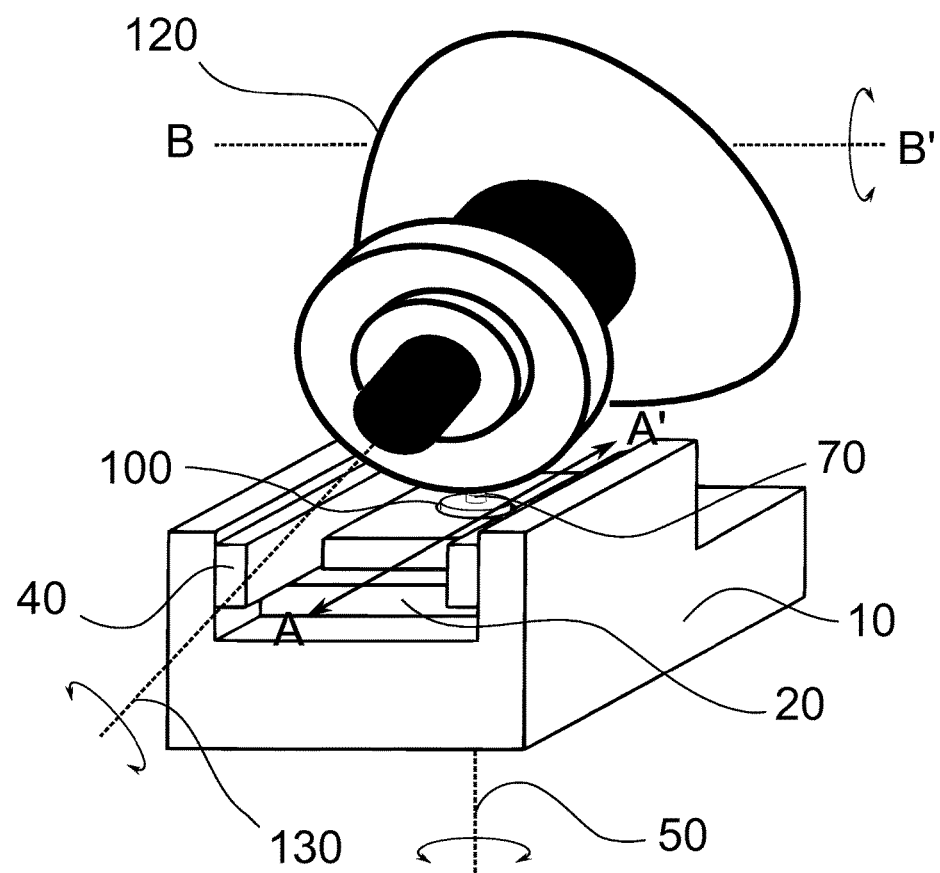
FIG. 3 a schematic diagram of a sample holder according to the invention for a sample 70 with an installed grinding unit 120.

FIG. 3 shows a schematic representation of a sample holder according to the invention for a sample 70 with a mounted grinding unit 120. The association of the reference numerals as well as of the functional relationships of the individual components corresponds largely to the description of FIGS. 1a, 1b and 2. An illustration of the disc 60 and the drive wheel 80 has been omitted. Evident is the slightly protruding sample pad 100 with the mounted sample 70 inserted in the carriage 20. According to the invention, the carriage performs a preferably linear movement along the direction A-A'. A grinding unit 120 disposed above the sample holder is schematically shown in a preferred orientation with respect to the surface of the sample 70. The grinding unit 120 includes a grinding wheel which rotates at a high speed about an axis of rotation 130 and continuously removes material from the sample 70 at an ideally singular point of contact at a certain angle. This angle may be freely changed, for example, by pivotally supporting the grinding unit 120, schematically indicated here by way of example with reference to an axis of rotation B-B'. The depicted spatial orientation of the axis of rotation 130 of the grinding unit 120 includes an angle of approximately 45° with respect to the axis of rotation 50 of the disc 60 and/or perpendicular to the axis of rotation 75 of the drive wheel 80.

Figure 4:
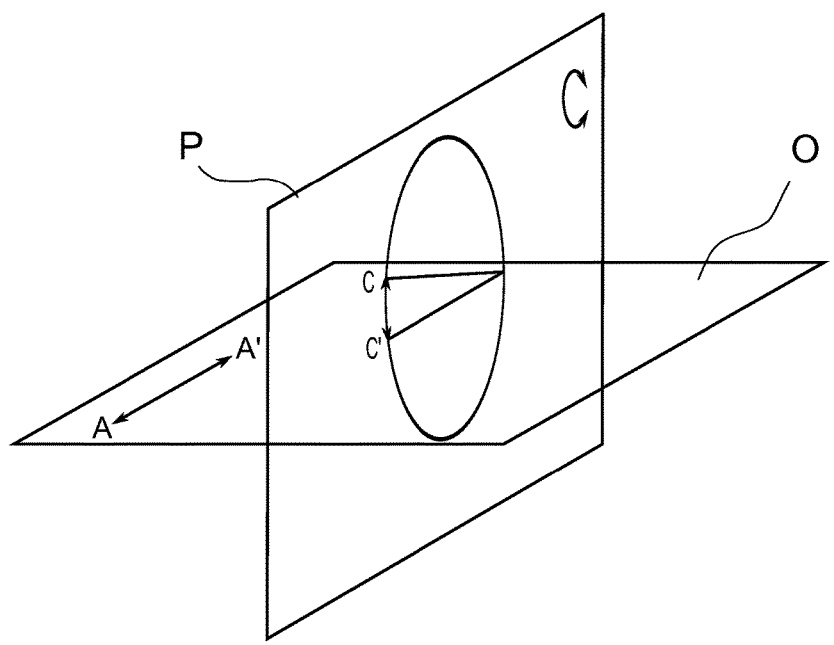
FIG. 4 a diagram of the reference planes O, P.

FIG. 4 shows a diagram of the corresponding reference planes O and P. The surface of the sample 70 is moved translationally in the plane O. Preferably, this involves an oscillating linear movement along the direction A-A'; however, in another preferred embodiment, this movement can also be performed on arbitrarily curved paths in the plane O. The grinding unit 120 hereby moves in a plane P perpendicular thereto. In particular, a possible movement of the axis of rotation of the grinding wheel in the plane P in the direction C-C' is shown. The implementation of the sample holder according to the invention is not restricted in any way to the association of planes illustrated here. In particular, the illustrated planes may for example also be arbitrarily tilted with respect to one another in space or the movements may occur on a free trajectory in space.

Figure 5:
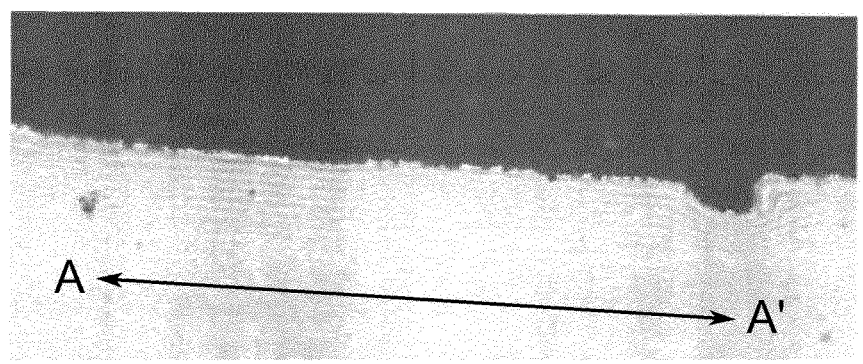
FIG. 5 the interference fringes of a sample edge generated with a sample holder according to the invention for a sample 70.

FIG. 5 shows the interference fringes at a sample edge of a sample 70 generated with the sample holder according to the invention. The carriage was hereby moved in the sample carrier with a linear oscillating movement, so that the grinding operation was carried out along the indicated direction A-A'. At the wedge-shaped grinding edge, the thickness of the sample increases continuously perpendicular to the grinding direction from the dark area. With achievable minimum thicknesses down to the nanometer range, interference fringes that are more or less linearly arranged in the grinding direction can be observed when the samples to be prepared are illuminated. This system allows simple conclusions about the already attained level of thinning and the quality of the prepared sample. This can also be established in silicon on the basis of the occurring characteristic red coloration of the sample material during optical inspection with light. A very homogeneous thinning of the edge along the direction of movement of the carriage can be inferred from the parallel linear interference fringe pattern. The variable relative spacing of the individual interference fringes also allows conclusions about the wedge-shaped profile of the abraded material produced by the grinding wheel.

To check the results from the desired sample preparation, different series of tests were performed on the samples that were thinned in a wedge-shape with the sample holder of the invention. Since an extensive know-how with respect to the underlying grinding and polishing processes for trough grinding on various sample materials is already available in the prior art, the corresponding procedures can be largely adapted here. By taking these material-specific properties into account, locations could be found on all samples examined so far, which were sufficiently thinned and are suitable for TEM images, in particular for high-resolution HRTEM images having a resolution limit of 0.2 nm.

LIST OF REFERENCE NUMBERS 10 supporting base
20 carriage
30 receiving region
40 guide
50 axis of rotation
60 rotatable disc
65 a center of the rotatable disc
70 sample
75 second axis of rotation
80 rotatable drive wheel
85 a center of the rotatable drive wheel
90 rotary drive
100 sample pad
110 opening of the carriage
111 opening the rotatable disc
112 opening of the drive wheel
114 viewing channel
120 grinding unit
130 axis of rotation of the grinding wheel
A, A' movement direction of the carriage
B, B' pivot axis of the grinding unit
C, C direction of the axis of rotation of the grinding wheel
O first plane
P second plane

The invention claimed is:

1. Sample carrier for a sample, comprising:
a supporting base;
a carriage having a receiving region for the sample, wherein the carriage is supported on the supporting base;
a guide, wherein the carriage is arranged for movement along the guide; and
a disc operatively connected to the carriage and rotatable about an axis of rotation, wherein a center of the disc is located outside the axis of rotation,
characterized in that
the carriage has an opening in its receiving region, wherein a sample pad is arranged in the opening, the sample pad being transparent in at least one optical spectral range;
the disc has an opening; and
a drive wheel has an opening, wherein a common axis as a visual axis runs through the opening of the carriage, through the opening of the disc and through the opening of the drive wheel.

2. Sample carrier of claim 1, wherein the drive wheel is rotatable about a second axis of rotation and operatively connected to the disc, and wherein a center of the drive wheel is located on the axis of rotation of the disc.

3. Sample carrier of claim 2, wherein the axis of rotation of the rotatable disc coincides with the axis of rotation of the drive wheel.

4. Sample carrier of claim 2, wherein the drive wheel is operatively connected with a rotary drive.

5. Sample carrier of claim 1, wherein the disc or the drive wheel comprise at least partly a magnetic material.

6. Sample carrier of claim 1, wherein the carriage or the guide comprise a non-magnetic material.

7. Sample carrier of claim 1, wherein the sample pad is formed entirely of an optically transparent material.

8. Sample carrier of claim 1, wherein the sample pad protrudes from the opening of the carriage.

9. Device for processing a sample comprising a sample carrier according to claim 1 and a grinding unit.

10. Device of claim 9, wherein an axis of rotation of the grinding unit encloses an angle of greater than 10° with the axis of rotation of the rotatable disc or perpendicular to the axis of rotation of the drive wheel.

11. Method for processing a sample, comprising:
providing a device for processing a sample according to claim 9;
placing a sample on the sample pad;
translationally moving the sample in a first plane; and grinding the sample, wherein the grinding unit is moved in a second plane, wherein the second plane encloses an angle of greater than 50° with the first plane.

\* \* \* \* \*